(12) United States Patent
Wen et al.

(10) Patent No.: US 9,869,643 B2
(45) Date of Patent: Jan. 16, 2018

(54) MASKS THAT SELECTIVELY ATTENUATE RADIATION FOR INSPECTION OF PRINTED CIRCUIT BOARDS

(71) Applicant: Cisco Technology, Inc., San Jose, CA (US)

(72) Inventors: ShiJie Wen, Sunnyvale, CA (US); Richard J. Wong, Saratoga, CA (US)

(73) Assignee: Cisco Technology, Inc., San Jose, CA (US)

( * ) Notice: Subject to any disclaimer, the term of this patent is extended or adjusted under 35 U.S.C. 154(b) by 302 days.

(21) Appl. No.: 14/163,756

(22) Filed: Jan. 24, 2014

(65) Prior Publication Data
US 2015/0212217 A1   Jul. 30, 2015

(51) Int. Cl.
*G01N 23/02*   (2006.01)

(52) U.S. Cl.
CPC ....... *G01N 23/02* (2013.01); *G01N 2223/313* (2013.01); *G01N 2223/314* (2013.01); *G01N 2223/6113* (2013.01); *G01N 2223/646* (2013.01)

(58) Field of Classification Search
CPC ........... G01N 23/02; G01N 2223/6113; G01N 2223/646
See application file for complete search history.

(56) References Cited

U.S. PATENT DOCUMENTS

| 4,497,062 A * | 1/1985 | Mistretta | G21K 1/10 378/158 |
| 5,493,594 A * | 2/1996 | Hamada | G01N 23/04 378/34 |
| 7,453,987 B1 * | 11/2008 | Richardson | G01V 5/0041 378/57 |

(Continued)

FOREIGN PATENT DOCUMENTS

JP   1999326242 A1 * 11/1999 ............. G01B 15/00

OTHER PUBLICATIONS

Machine translation of JP1999326242A1 which was published in 1999.*

(Continued)

*Primary Examiner* — Glen Kao
(74) *Attorney, Agent, or Firm* — Patterson + Sheridan, LLP

(57) ABSTRACT

Masks that selectively attenuate radiation for inspections of printed circuit boards (PCB) are disclosed. A PCB may be inspected for defects by exposing the PCB with radiation and analyzing the radiation transmitted through the PCB. By employing a radiation mask having first and second segments between the PCB and a radiation source, the radiation may be selectively attenuated to attenuate a first portion of the radiation with a first attenuation level to prevent performance degradation to sensitive semiconductor devices as part of a first sectional area of the PCB, and yet provide substantially non-attenuation or attenuation at a second (Continued)

attenuation level for a second portion of the radiation incident upon a second sectional area of the PCB which is free from sensitive semiconductor devices. In this manner, the selective attenuation enables inspection of the first and second sectional areas of the PCB without damage to the sensitive semiconductor devices.

15 Claims, 9 Drawing Sheets

(56) References Cited

U.S. PATENT DOCUMENTS

| 2007/0206726 A1* | 9/2007 | Lu | G01N 23/203 |
| | | | 378/146 |
| 2011/0075815 A1* | 3/2011 | Brown | A61N 5/1048 |
| | | | 378/125 |
| 2013/0108024 A1 | 5/2013 | Parsons et al. | |

OTHER PUBLICATIONS

<https://web.archive.org/web/20130109124611/http://en.wikipedia.org/wiki/Printed_circuit_board>, Jan. 9, 2013.*

* cited by examiner

MASKS THAT SELECTIVELY ATTENUATE RADIATION FOR INSPECTION OF PRINTED CIRCUIT BOARDS

TECHNICAL FIELD

Embodiments presented in this disclosure generally relate to radiation inspection of electronic assemblies, and more specifically to radiation inspection of printed circuit boards to detect defects.

BACKGROUND

Recent advances in microelectronic design and integrated circuit fabrication techniques have enabled advanced design rule integrated circuits and other components to be incorporated as part of electronic assemblies, such as printed circuit boards. When integrated circuits or other components are incorporated as part of larger electronic assemblies, inspection processes may be included as part of the manufacturing process to ensure that the electronic assembly is free from defects such as missing or non-compliant electrical connections between components on the larger electronic assembly. In this regard, x-ray inspection machines may be used to ensure that the electronic assembly is defect-free, but sometimes radiation inspection is avoided in favor of other defect-reduction approaches because radiation may cause defects in the electronic assemblies being inspected. Specifically, X-ray radiation may adversely change materials used in electronic assemblies.

Avoiding the use of X-ray inspection has been difficult, because as critical dimension sizes of electrical components further decrease with each successive generation, these components are becoming more sensitive to radiation. Further, with advancements in technology it has become increasingly difficult to design more densely-packed electronic assemblies and to provide inspection solutions ensuring reliability and performance without exposing components to damaging radiation. New approaches are needed to ensure defect-free electronic assemblies without causing reliability or performance issues associated with inspection radiation damage.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DESCRIPTION OF EXAMPLE EMBODIMENTS

Overview

Figure 1:
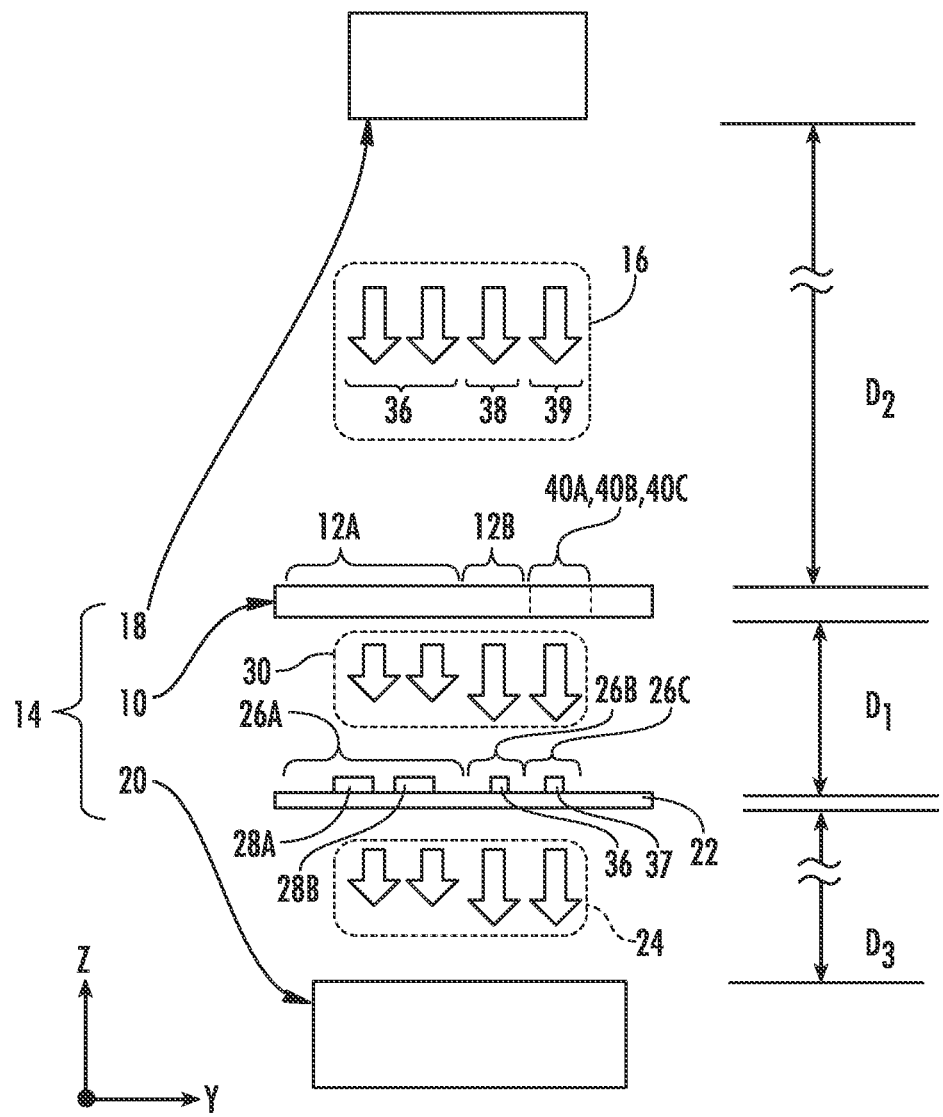
FIG. 1 is a schematic view of an exemplary radiation mask having a first sectional area and a second sectional area being employed as part of a printed circuit board (PCB) inspection system to selectively attenuate radiation from a radiation source, and the radiation mask being disposed between the radiation source and an exemplary PCB, according to one embodiment described herein.

In one embodiment, an exemplary method for inspecting a printed circuit board (PCB) is disclosed. The method may include providing a PCB comprising a first sectional area including at least one sensitive semiconductor device, and a second sectional area is free of a sensitive semiconductor device. The method may also include disposing a radiation mask between a radiation source and the PCB, the radiation mask including a first segment and a second segment. The method may also include emitting, from the radiation source, a first portion of radiation towards the first sectional area and a second portion of the radiation towards the second sectional area. The first portion passes through the first segment that attenuates the first portion at a first attenuation level, and the second portion passes through the second segment substantially non-attenuated or attenuated at a second attenuated level less than the first attenuation level. The method may also include receiving, with a defect identification unit, a transmitted portion of the radiation that passed through the PCB. In this manner, defects in the PCB may be detected by the defect identification unit while avoiding performance degradation of the at least one sensitive semiconductor device of the PCB.

In another embodiment, an inspection system for a PCB is disclosed. The system may include a radiation source configured to emit radiation towards the PCB. The system may also include a radiation mask disposed between the radiation source and the PCB. The radiation mask may include a first segment configured to pass through the first segment a first portion of the radiation emitted towards a first sectional area of the PCB. The first segment may be configured to attenuate the first portion with a first attenuation level. The first sectional area of the PCB includes at least one sensitive semiconductor device. The radiation mask may also include a second segment configured to receive a second portion of the radiation emitted towards a second sectional area of the PCB. The second segment may be configured to pass through the second segment the second portion substantially non-attenuated or attenuated at a second attenuation level. The second attenuation level may be less than the first attenuation level. The second sectional area of the PCB is free of a sensitive semiconductor device. The system may also include a defect identification unit configured to receive a transmitted portion of the radiation that passed through the PCB. In this manner, defects may be reduced for electronic assemblies containing at least one semiconductor device which may be sensitive to inspection radiation.

In another embodiment, a radiation mask for a PCB inspection system is disclosed. The radiation mask may include a first segment configured to pass a first portion of radiation emitted towards a first sectional area of a PCB. The first segment may be configured to attenuate the first portion with a first attenuation level. The first sectional area of the PCB includes at least one sensitive semiconductor device. The radiation mask may also include a second segment configured to pass a second portion of the radiation emitted towards a second sectional area of the PCB. The second segment may be configured to substantially non-attenuate or attenuate at a second attenuation level the second portion of the radiation. The second attenuation level may be less than the first attenuation level. The second sectional area of the PCB is free of a sensitive semiconductor device. In this manner, radiation from the PCB inspection system may be attenuated to prevent performance degradation to semiconductor devices and yet inspection may be utilized to identify defects that may occur.

Example Embodiments

Embodiments disclosed herein include masks that selectively attenuate radiation for inspections of printed circuit boards (PCB). A PCB may be inspected for defects by exposing the PCB with radiation and analyzing the radiation transmitted through the PCB. By employing a radiation mask having first and second segments between the PCB and a radiation source, the radiation may be selectively attenuated to attenuate a first portion of the radiation with a first attenuation level to prevent performance degradation to sensitive semiconductor devices as part of a first sectional area of the PCB, and yet provide substantially non-attenuation or attenuation at a second attenuation level for a second portion of the radiation incident upon a second sectional area of the PCB which is free from sensitive semiconductor devices. In this manner, the selective attenuation enables inspection of the first and second sectional areas of the PCB without damage to the sensitive semiconductor devices.

FIG. 1 is a schematic view of an exemplary radiation mask 10 having a first segment 12A and a second segment 12B being employed as part of a printed circuit board (PCB) inspection system 14 to selectively attenuate radiation 16 emitted from a radiation source 18. In one embodiment, for example, the radiation 16 may be X-rays having energy in a range from five (5) keV to one-hundred sixty (160) keV. The PCB inspection system 14 includes the radiation mask 10, the radiation source 18, and a defect identification unit 20. A PCB 22 to be inspected is disposed between the defect identification unit 20 and the radiation source 18. A transmitted portion 24 of the radiation 16 emitted by the radiation source 18 may be transmitted through the PCB 22 and received by the defect identification unit 20. Some of the radiation 16 may not reach the defect identification unit 20 as the transmitted radiation 24 because some of the radiation 16 may instead be, for example, absorbed by or reflected from the PCB 22 or the radiation mask 10. Once the transmitted portion 24 of the radiation 16 is received by the defect identification unit 20, sensors and electronics (not shown) may analyze the transmitted portion 24 to determine whether the PCB 22 contains defects which may be detectable by the defect identification unit 20 by altering an amount of the radiation 16 transmitted though the PCB 22 and received by the defect identification unit 20. In this manner, defects of the PCB 22 may be identified.

The defect identification unit 20 may identify various defects of the PCB 22 even though the radiation mask 10 may be disposed between the radiation source 18 and the PCB 22. The radiation mask 10 may selectively attenuate the radiation 16, so that in one embodiment, the first segment 12A of the mask 10 may attenuate the first portion 36 of the radiation 16 at a first attenuation level as the first portion 36 passes through the first segment 12A of the radiation mask 10 to be incident upon the first sectional area 26A of the PCB 22. Moreover, the second segment 12B of the mask 10 may provide substantially non-attenuation or attenuation at a second attenuation level for the second portion 38 of the radiation 16 as the second portion 38 passes through the second segment 12B of the radiation mask 10 to be incident upon the second sectional area 26B of the PCB 22. The second attenuation level may be less than the first attenuation level. Accordingly, by selectively attenuating the radiation 16, damage to the at least one sensitive semiconductor device 28A, 28B at the first sectional area 26A of the PCB 22 may be avoided yet inspection may still occur at the second sectional area 26B. In this regard, the term "sensitive semiconductor device" as used herein means a semiconductor device which forms traps (or voids) in oxides surrounding individual transistors when exposed to the radiation 16 (in a substantially non-attenuated exposure) and these traps or voids affect performance characteristics of the transistors.

With continued reference to FIG. 1, the sensitive semiconductor devices 28A, 28B may be located in the first sectional area 26A of the PCB 22. In contrast, other electronic components and connections (not shown) which are less sensitive to the radiation 16 may be located in the second sectional area 26B and may be susceptible to defects which may be identifiable with at least a second portion 38 of the radiation 16 and the defect identification unit 20. The ability to detect defects in the second sectional area 26B may be impaired if the second portion 38 of the radiation 16 were substantially attenuated to the same extent as the first portion 38 of the radiation 16. Accordingly, substantially non-attenuation or a second level of attenuation may be used to provide more effective inspection in the second sectional area 26B of the PCB 22. Thus, being able to selectively attenuate the radiation 16 before the radiation 16 reaches the PCB 22 may reduce performance degradations to the sensitive semiconductor device 28A, 28B in the first sectional area 26A of the PCB 22, yet still enable inspection of the second sectional area 26B of the PCB 22.

In other words, a first portion 36 of the radiation 16 incident upon the first segment 12A of the radiation mask 10 may be attenuated at the first attenuation level to accommodate a specified degree of defect inspection capability and radiation sensitivity of the first sectional area 26A of the PCB 22. The term "first attenuation level" as used herein means blocking from the PCB 22 more than seventy-five (75) percent of the dose exposure of the radiation 16 having an energy level in a specified energy range from five (5) KeV to one-hundred sixty (160) KeV. In contrast, the second portion 38 of the radiation 16 incident upon the second segment 12B of the radiation mask 10 may pass through the second segment 12B with a second attenuation level to accommodate a specified degree of defect inspection capability and radiation sensitivity of the second sectional area 26B of the PCB 22. The term "second attenuation level" as used herein means blocking from the PCB 22 from ten (10) percent to at least seventy-five (75) percent of the dose exposure of the radiation 16 having an energy level in the specified energy range from five (5) KeV to one-hundred sixty (160) KeV. The term "substantially non-attenuated" as used herein means blocking from the PCB 22 less than ten (10) percent of the dose exposure of the radiation 16 having an energy level in the specified energy range from five (5) KeV to one-hundred sixty (160) KeV. The energy level of the radiation 16 in the specified energy range from five (5) KeV to one-hundred sixty (160) KeV may be used herein to demarcate differences between the first attenuation level, the second attenuation level, and substantially non-attenuation because this specified energy range may be most damaging to the sensitive semiconductor devices 28A, 28B.

With continued reference to FIG. 1, selective attenuation may be provided by the radiation mask 10 to the PCB 22 by several factors including a distance $D_1$ of the radiation mask 10 from the PCB 22, a distance $D_2$ of the radiation mask 10 from the radiation source 18, shapes of the first sectional area 12A and the second sectional area 12B of the radiation mask 10, and materials and thicknesses of the first sectional area 26A and the second sectional area 26B of the radiation mask 22. These factors are now discussed in turn.

As to the distance $D_1$, the radiation mask 10 may be disposed proximate to the PCB 22 and at the distance $D_1$ away to minimize divergent effects of imperfect collimation of the radiation 16. The divergent effects include a portion 36 of the radiation 16 incident upon the first segment 12A becoming incident upon both the first and second sectional area 26A, 26B of the PCB 22, and a portion 38 of the radiation 16 transmitted through the second segment 12B of the radiation mask 10 also being incident upon the first and second sectional areas 26A, 26B of the PCB 22. In order to accommodate both collimated and non-collimated components of the radiation 16 to minimize the divergent effects, the distance $D_1$ may be minimized. For example, the distance $D_1$ may be in a range from two millimeters to fifteen (15) millimeters. In this manner, the divergent effects of the radiation 16 may be minimized.

As to the distance $D_2$ between the radiation source 18 and the radiation mask 10, increasing the distance $D_2$ may reduce the opportunity for non-collimated portions of the radiation 16 to be incident upon the radiation mask 10 as non-collimated rays are allowed to propagate away from the radiation mask 10. The distance $D_2$ may be greater than ten (10) millimeters in order minimize an opportunity for highly divergent rays of the radiation 16 from contacting the radiation mask 10. In this way, the divergent effects of non-collimated portions of the radiation 16 may also be reduced.

Figure 2A:
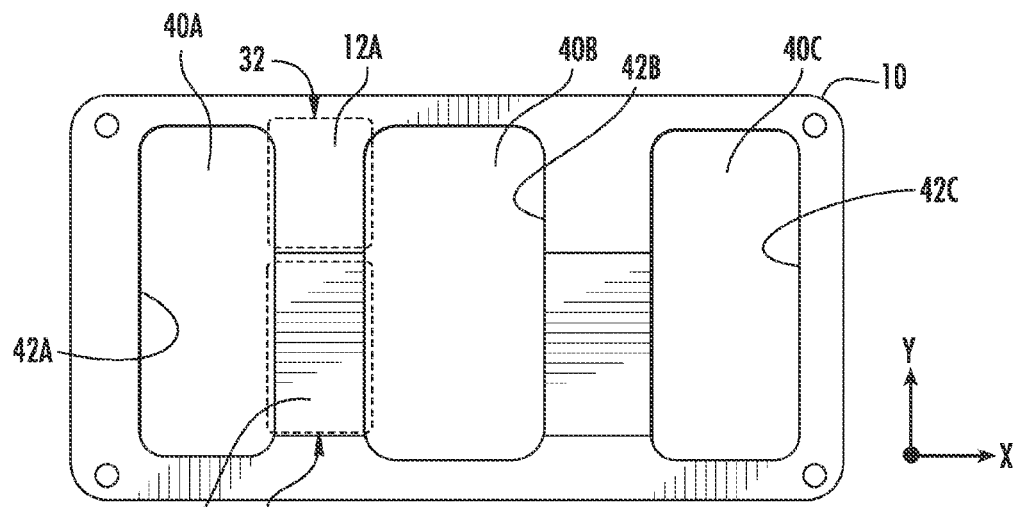
FIG. 2A is a top view of the radiation mask of FIG. 1, according to one embodiment described herein.
Figure 2B:
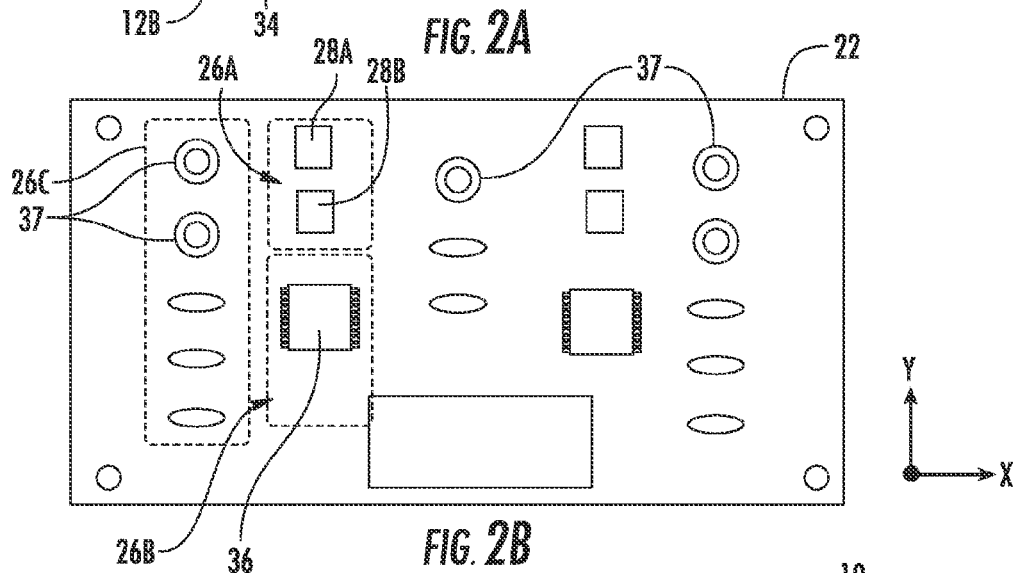
FIG. 2B is a top view of the PCB of FIG. 1, according to one embodiment described herein.
Figure 2C:
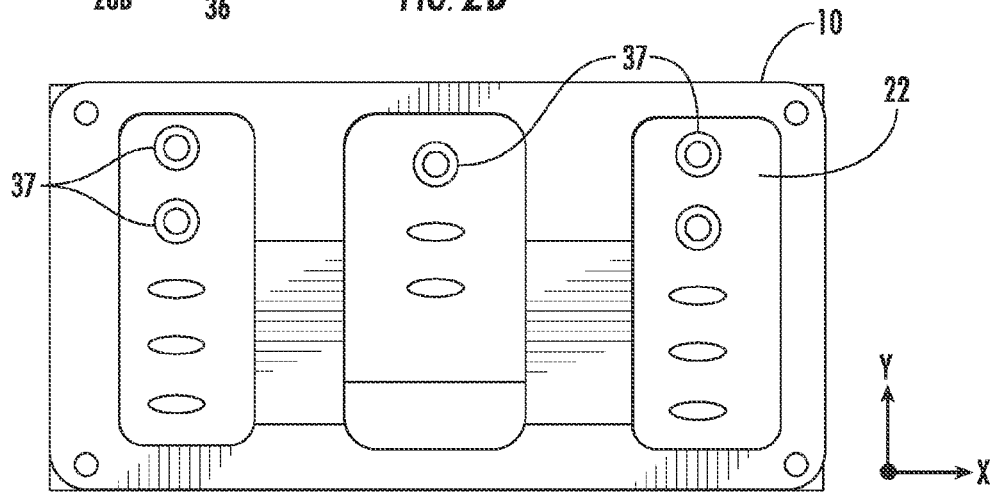
FIG. 2C is a top view of the radiation mask of FIG. 2A proximate to the PCB of FIG. 2B illustrating the PCB and the radiation mask being prepared for radiation inspection, according to one embodiment described herein.
Figure 3A:
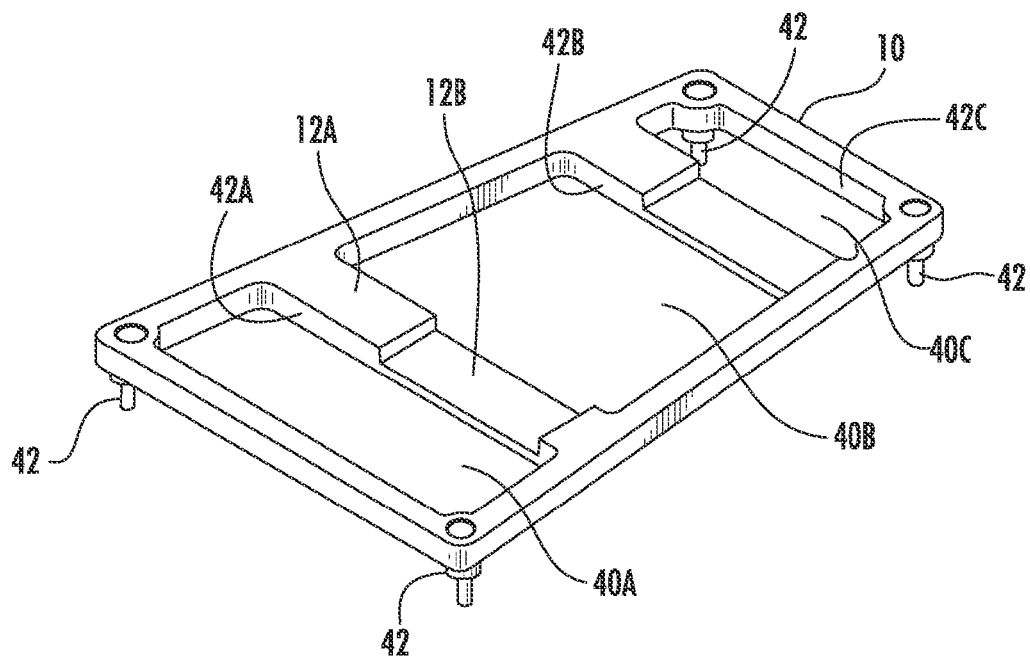
FIGS. 3A-3E are a top perspective view, top view, first side sectional view, second side sectional view, and exploded view, respectively, of the radiation mask of FIG. 1, according to one embodiment described herein.
Figure 3B:
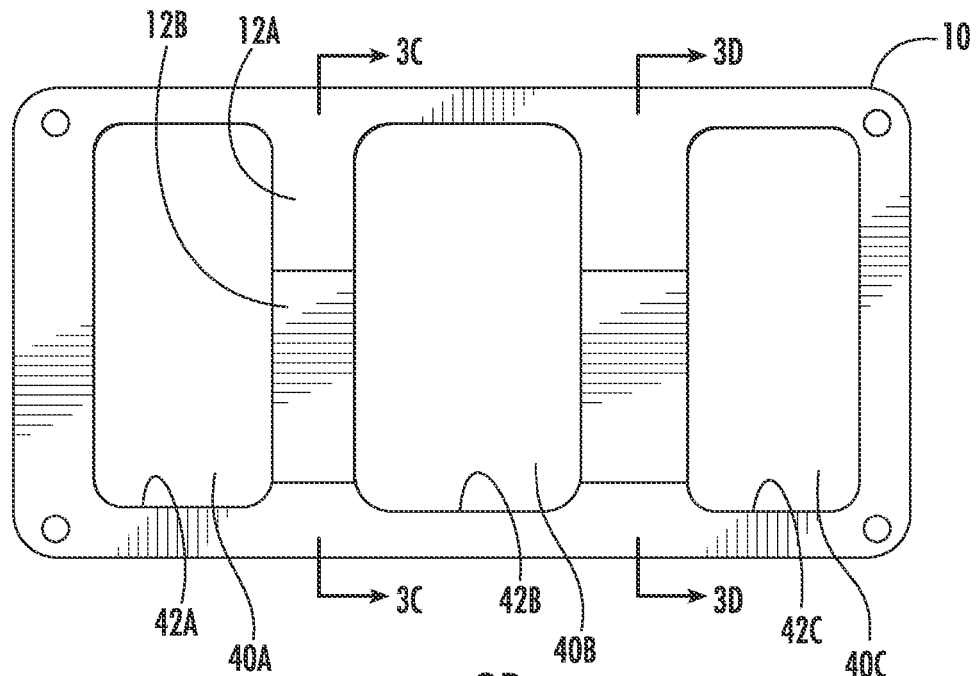
Figure 3C:
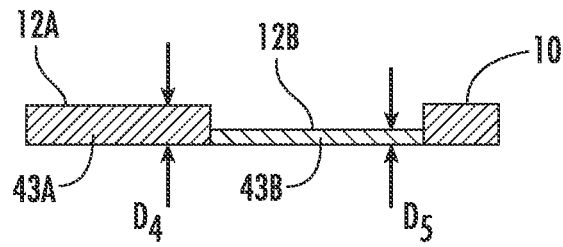
Figure 3D:
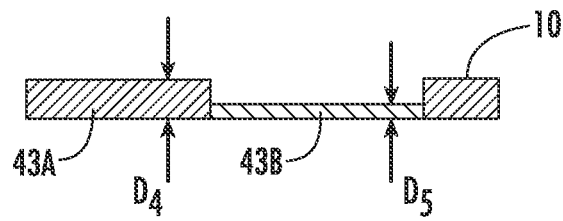
Figure 3E:
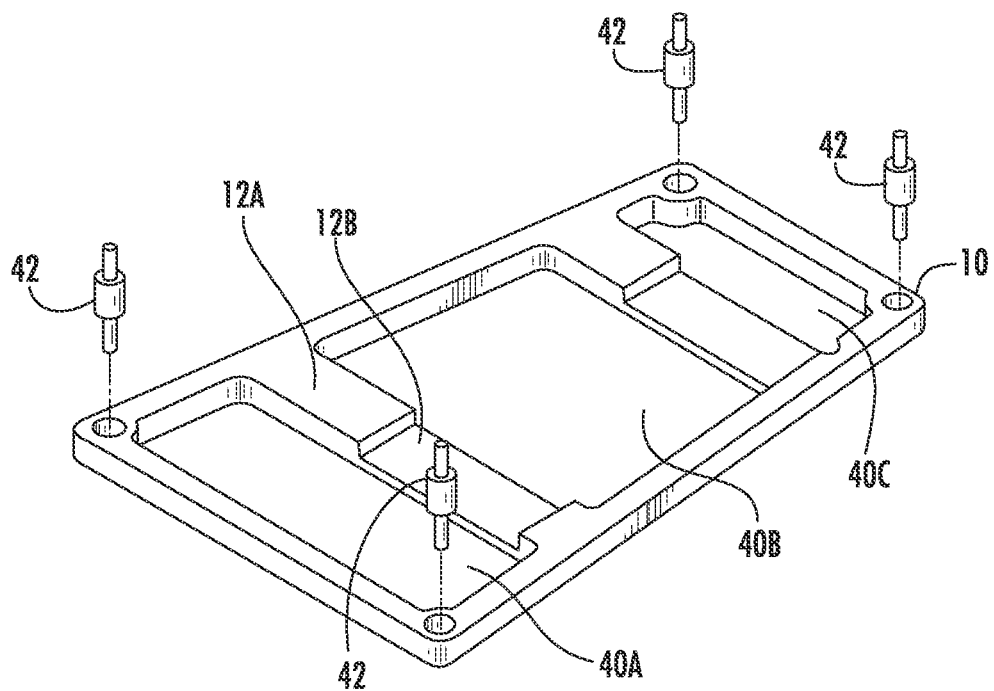

Next, FIGS. 2A through 2C depict top views, respectively, of the radiation mask 10, the PCB 22, and the radiation mask 10 disposed proximate to the PCB 22. In this regard, FIG. 2A depicts an exemplary radiation mask 10 including a shape 32 and a shape 34. The shape 32 of the first segment 12A of the radiation mask 10 corresponds to a relative location of a first sectional area 26A of the PCB 22 which contains the sensitive semiconductor devices 28A, 28B of the PCB 22 as shown in a top view of an exemplary PCB 22 as shown in FIG. 2B. In this way, the shape 32 may be configured so that a portion 36 (FIG. 1) of the radiation 16 may be selectively attenuated by the first segment 12A of the radiation mask 10 according to the radiation sensitivity and inspection needs of the first sectional area 26A of the PCB 10.

With continued reference to FIGS. 2A through 2C, the shape 34 of the second segment 12B of the radiation mask 10 corresponds to a relative location of the second sectional area 26B of the PCB 22 which may be free of a sensitive semiconductor device, but may contain an electronic device 36 which is relatively insensitive to the radiation 16. The shape 34 may be configured so that a portion 38 (FIG. 1) of the radiation 16 may be selectively attenuated by the second segment 12B of the radiation mask 10 according to the radiation sensitivity and inspection needs of the second sectional area 26B of the PCB 10. Accordingly, FIG. 2C is a top view of the radiation mask 10 of FIG. 2A disposed proximate to the PCB 22 of FIG. 2B illustrating the shapes 32, 34 of the segments 12A, 12B positioned to selectively attenuate the radiation 16 for the sectional areas 26A, 26B of the PCB 22. The relative locations of the first segment 12A and the second segment 12B to the first sectional area 26A and the second sectional area 26B are configured to selectively attenuate the radiation 16, so that the inspection requirements can be achieved and radiation damage avoided.

It is noted that the radiation mask 10 may also include at least one passageway 40A, 40B, 40C through the radiation mask 10. The passageways 40A, 40B, 40C may be formed from surfaces 42A, 42B, 42C, respectively, through the radiation mask 10. The passageways 40A, 40B, 40C may be aligned with a third sectional area 26C of the PCB 22 which may be in a path of a third portion 39 of the radiation 16. The third sectional area 26C may contain electronic elements 37 which may be relatively insensitive to the radiation 16, but may contain detectable defects. For example, the electronic elements 37 may comprise electronic traces of the PCB 22. In this way, the portion 39 of the radiation 16 may pass through the passageways 40A, 40B, 40C of the radiation mask 10 to the PCB 22 substantially non-attenuated by the radiation mask 10 to provide a highest intensity and energy level of the radiation 16 for enhanced defect detection in the third sectional area 26C of the PCB 22.

FIGS. 3A-3E are a top perspective view, top view, first side sectional view, second side sectional view, and exploded view, respectively, of the radiation mask of FIG. 2A illustrating details of the radiation mask 10, including different materials and thicknesses that may be used to selectively attenuate the radiation 16. For example, as shown in first side sectional view in FIG. 3C, the radiation mask 10 may include a first material 43A of first segment 12A. Further, the radiation mask 10 may include a second material 43B of second segment 12B. The first material 43A may comprise one or more of lanthanum, cerium, gold, tungsten, tin, bronze, lead, and copper. The second material 43B may comprise, relative to the first material 43A, a different one or different combination of lanthanum, cerium, gold, tungsten, tin, bronze, lead, and copper. Different materials may have different attenuation characteristics. In this manner, the selective attenuation through the first segment 12A and the second segment 12B of the radiation mask 10 may be provided by adjusting respective ones of the materials to accommodate a specified degree of defect inspection capability and radiation sensitivity of the first sectional area 26A of the PCB 22 and the second sectional area 26B of the PCB 22.

With continued reference to FIGS. 3A-3E, different thicknesses may be used to selectively attenuate the radiation 16. For example, as shown in first side sectional view of the radiation mask 10 in FIG. 3C, the radiation mask 10 may include a thickness $D_4$ of first segment 12A. Further, the radiation mask 10 may include a thickness $D_5$ of second segment 12B. The radiation 16 may be more attenuated when incident upon a thicker material than a thinner material. In this regard, the first thickness $D_4$ may be in a range from two hundred (200) microns to fifteen (15) millimeters. The second thickness $D_5$ may be in a range from two hundred (200) microns to fifteen (15) millimeters and may be the same or a different thickness than the thickness $D_4$. In this manner, the selective attenuation through the first section 12A and the second section 12B of the radiation mask 10 may be provided by adjusting the thicknesses $D_4$, $D_5$ to accommodate a specified degree of defect inspection capability and radiation sensitivity of the first sectional area 26A of the PCB 22 and the second sectional area 26B of the PCB 22.

Figure 4A:
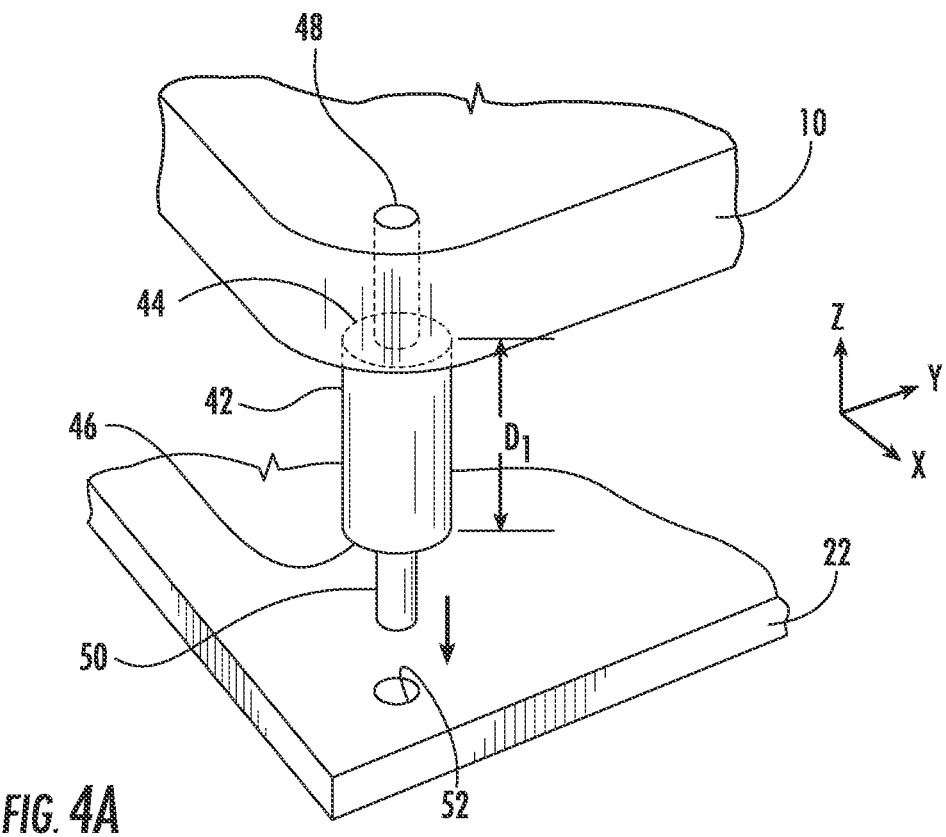
FIGS. 4A and 4B are partial top perspective views of the radiation mask of FIG. 1 interfacing and interfaced, respectively, with the PCB of FIG. 1, according to one embodiment described herein.
Figure 4B:
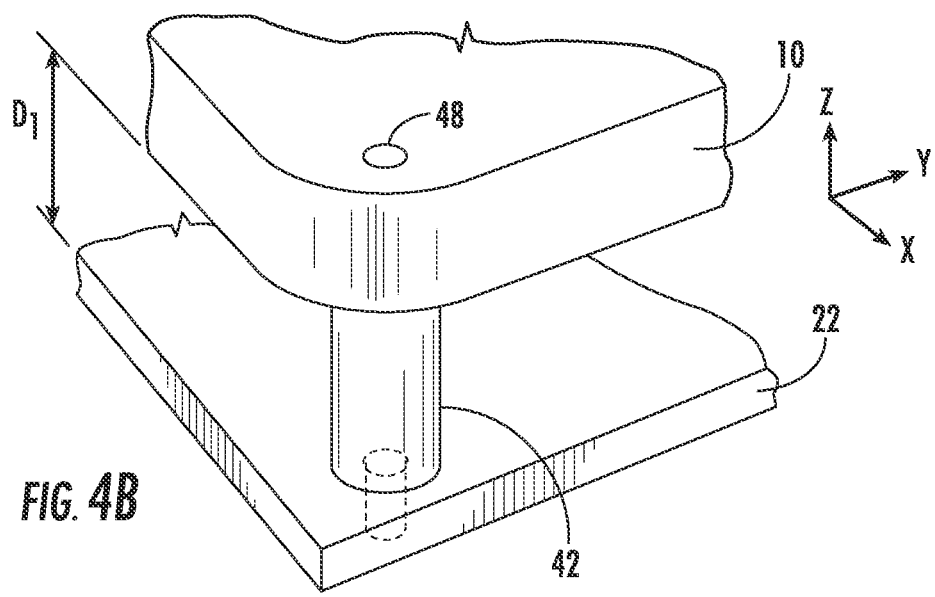

Now that the composition and dimensional characteristics have been introduced, an embodiment of disposing the radiation mask 10 proximate to the PCB 22 is now discussed. In this regard, FIGS. 4A and 4B are partial top perspective views of the radiation mask 10 of FIG. 1 interfacing and interfaced, respectively, with the PCB 22 of FIG. 1 using at least one standup pin 42. The standup pin 42 may include a first surface 44 configured to abut against the radiation mask 10 and a second surface 46 configured to abut against the PCB 22. The first surface 44 and the second surface 46 may be separated by the distance $D_1$. The standup pin 40 may be composed of a strong resilient material, for example, metal or plastic to keep the radiation mask 10 separated the distance $D_1$ from the PCB 22.

The standup pin 42 may be attached to the radiation mask 10 using a fastener 48. In various embodiments, the fastener 48 may comprise a threaded protrusion or may be integrally formed as part of the radiation mask 10. The standup pin 40 may be removably attached with the PCB 10, for example in one embodiment may include a protrusion 50 extending from the second surface 46. The protrusion 50 may be interfaced with at least one interface surface 52 of the PCB 22 to removably interface the radiation mask to the PCB 22. The at least one interface surface 52 of the PCB 22, in one non-limiting embodiment, may form a hole through the PCB 22. In this manner, the radiation mask 10 may be disposed proximate to the PCB 22.

Figure 5:
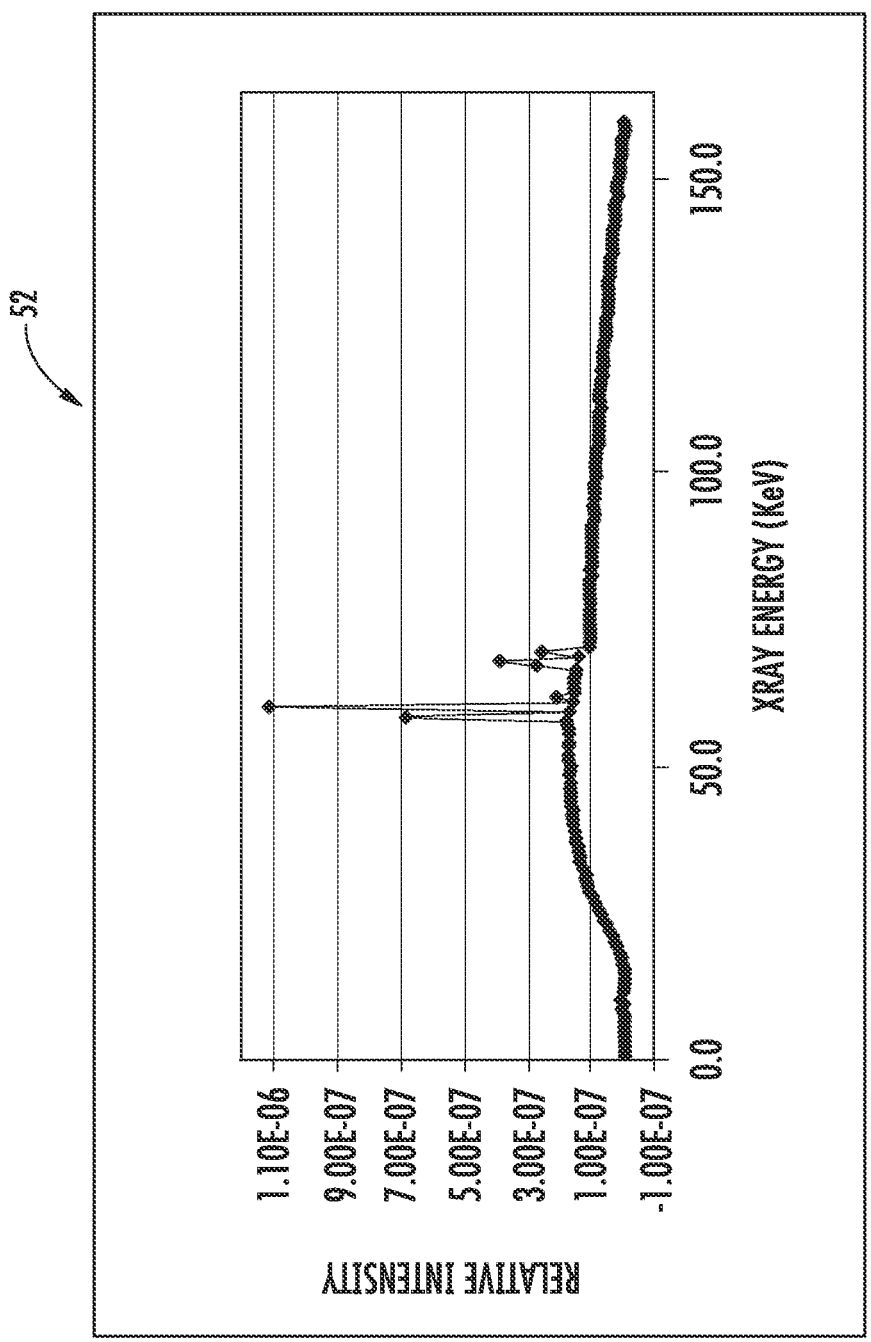
FIG. 5 is a graph of a relative intensity of the radiation emitted from the radiation source of FIG. 1 as a function of radiation energy, according to one embodiment described herein.
Figure 6:
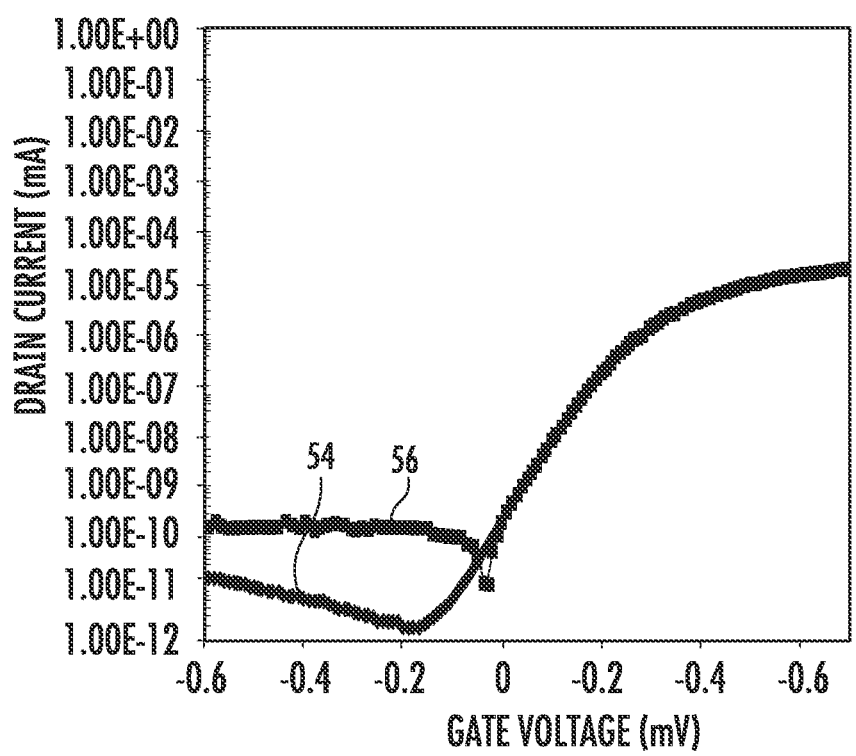
FIG. 6 is a graph of drain current versus voltage for an exemplary transistor of at least one sensitive semiconductor device of the PCB in FIG. 1, illustrating damage incurred from radiation inspection, according to one embodiment described herein.

Now that the radiation mask 10 has been discussed and one embodiment has been introduced to dispose the radiation mask 10 proximate to the PCB 22, empirical results are now discussed. FIG. 5 is a graph 52 of a relative intensity of the radiation 16 emitted from the radiation source 18 of FIG. 1 as a function of radiation energy. When exemplary transistors of the semiconductor devices 28A, 28B are exposed to the radiation 16 having the relative intensity depicted in FIG. 5, measured drain current characteristics of these transistors as shown in FIG. 6 may change. Specifically, the drain current of a pre-radiation exposure characteristic 54 increases to a post-radiation exposure characteristic 56. By using the radiation mask 10 during inspection, the drain current characteristic can be maintained by adjusting the material and thickness of the first segment 12A and second segment 12B of the radiation mask 10 to prevent harmful radiation exposure causing changes to the drain current characteristics of the transistors.

Figure 7:
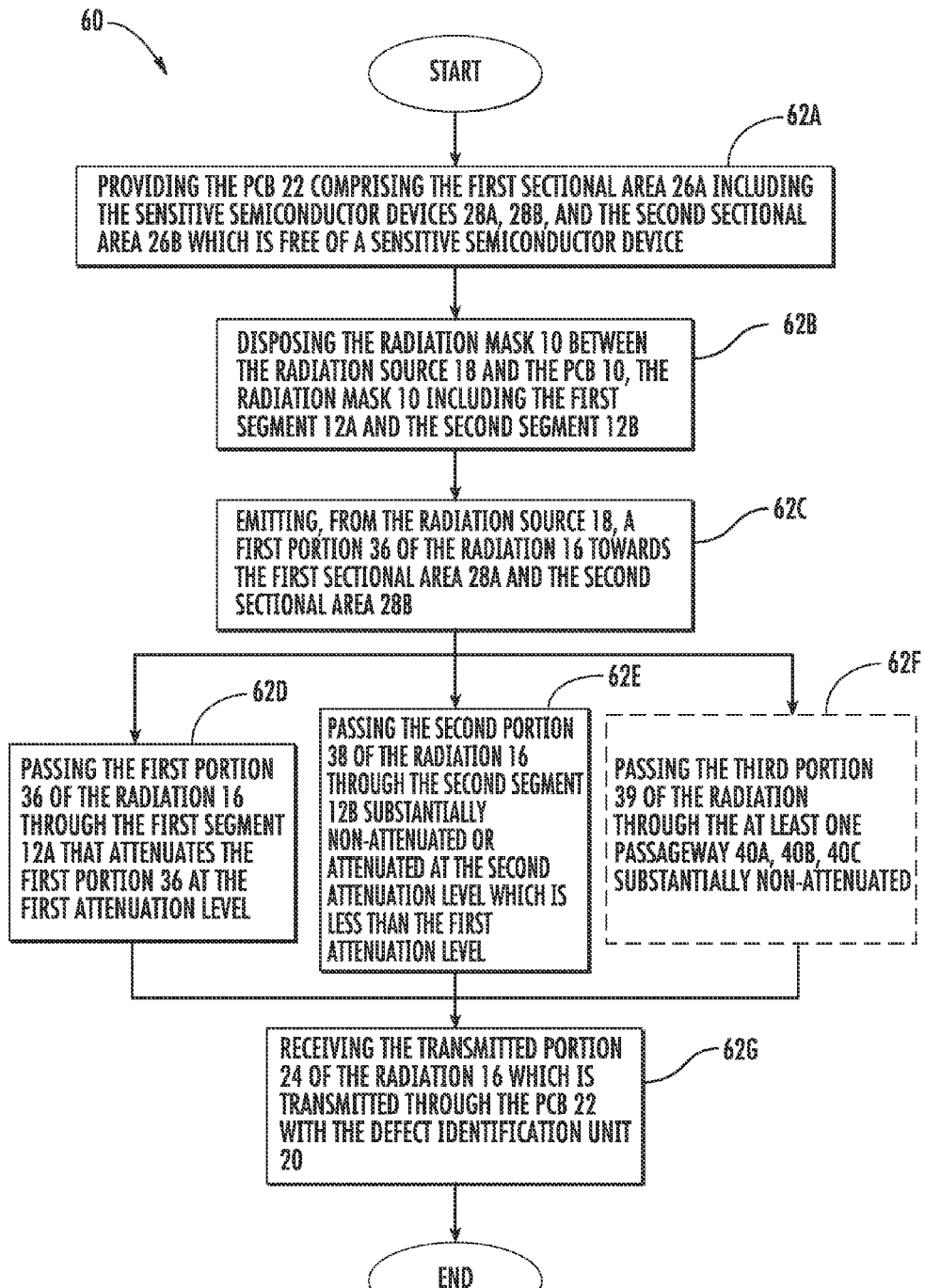
FIG. 7 is a flowchart diagram of an exemplary method for inspecting a printed circuit board using the PCB inspection system employing the radiation mask of FIG. 1, according to one embodiment described herein.

Now that details of the radiation mask 10 have been discussed as well as empirical data, FIG. 7 is a flowchart diagram of an exemplary method 60 for inspecting the PCB 22 is provided. The method 60 will be discussed using the terminology discussed above with respect to FIG. 7. In this regard, the method 60 may include providing the PCB 22 (Block 62A in FIG. 7). The PCB 22 may comprise the first sectional area 26A including the sensitive semiconductor devices 28A, 28B, and the second sectional area 26B which is free of a sensitive semiconductor device. In this manner, the PCB 22 may have areas which have differing vulnerability to damage from the radiation 16, but may have defects to be identified.

The method 60 may also include disposing the radiation mask 10 between the radiation source 18 and the PCB 10, the radiation mask 10 including the first segment 12A and the second segment 12B (Block 62B in FIG. 7). The first segment 12A of the radiation mask 10 may be disposed proximate to the first sectional area 26A of the PCB 22 and the second segment 12B of the radiation mask 10 may be disposed proximate to the second sectional area 26B of the PCB 22. The thickness $D_4$ of the first segment 12A may be thicker than the thickness $D_5$ of the second segment 12B. Further, block 62B may also include interfacing the at least one standup pin 42 of the radiation mask 10 with the PCB 22 and/or positioning the first segment 12A and the second segment 12B the distance $D_1$ from the PCB 22. In one embodiment, the thickness $D_4$ of the first segment 12A is based on an average drain current leakage change associated with the at least one sensitive semiconductor device 28A, 28B of less than one (1) percent resulting after at least two (2) radiation inspections.

The method 60 may also include emitting, from the radiation source 18, a first portion 36 of the radiation 16 towards the first sectional area 28A and the second sectional area 28B (Block 62C in FIG. 7). The radiation source 18 may emit the radiation 16 having energy in the energy range from five (5) KeV to one-hundred sixty (160) KeV. In this manner, the radiation 16 may be harmful to the sensitive semiconductor devices 28A, 28B, but yet may contain sufficient energy and the intensity to enable inspection of areas of the PCB 22 which are free from sensitive semiconductor devices.

The method 60 also includes passing the first portion 36 of the radiation 16 through the first segment 12A that attenuates the first portion 36 at the first attenuation level (Block 62D in FIG. 7). The method 60 also includes passing the second portion 38 of the radiation 16 through the second segment 12B substantially non-attenuated or attenuated at the second attenuation level which is less than the first attenuation level (Block 62E in FIG. 7). The method 60 may also include passing the third portion 39 of the radiation through the at least one passageway 40A, 40B, 40C substantially non-attenuated (Block 62F in FIG. 7). In this way, the radiation 16 may be selectively attenuated.

The method 60 may also include receiving the transmitted portion 24 of the radiation 16 which is transmitted through the PCB 22 with the defect identification unit 20 (Block 62G in FIG. 7). In this way, the first sectional area 26A and the second sectional area 26B of the PCB 22 may receive selectively attenuated amounts of the radiation 16.

Figure 8A:
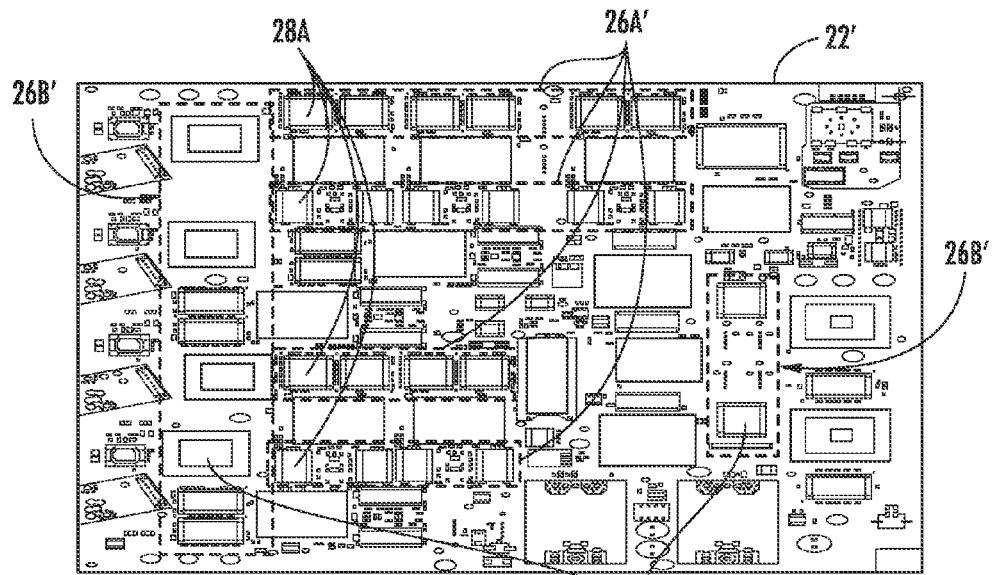
FIGS. 8A and 8B are top views, respectively, of another embodiment of a PCB, and another embodiment of a radiation mask to provide selective attenuation for the PCB of FIG. 8A, according to one embodiment described herein.
Figure 8B:
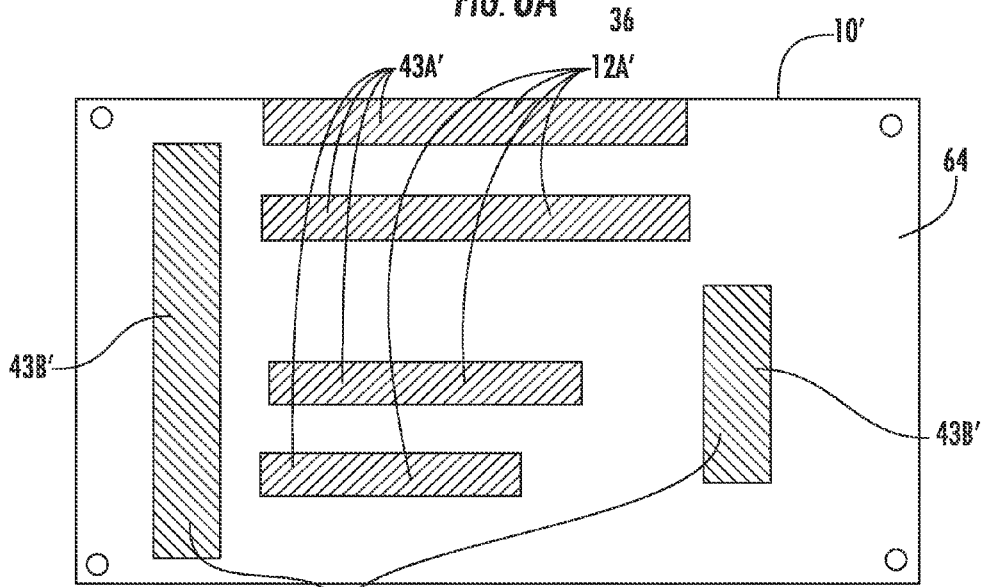
Figure 8C:
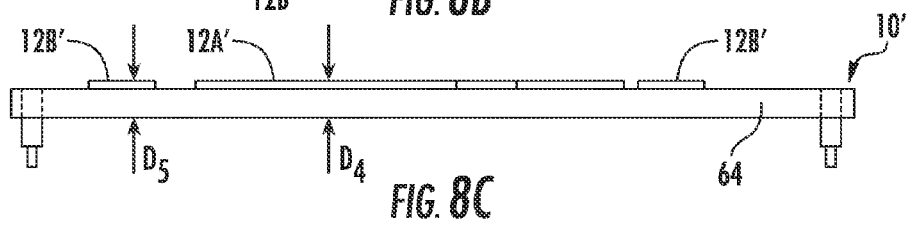
FIG. 8C is a side view of the radiation mask of FIG. 8B, according to one embodiment described herein.

FIGS. 8A and 8B are top views, respectively, of another embodiment of a PCB 22' and another embodiment of a radiation mask 10' consistent with radiation inspection of the PCB 22'. FIG. 8C is a side view of the radiation mask 10' of FIG. 8B. The radiation mask 10' and the PCB 22' are similar to the radiation mask 10' and the PCB 22 discussed above and so differences will be discussed in an effort for clarity and conciseness. The PCB 22' of FIG. 8A includes greater quantity of components than PCB 22 as may be consistent with later generation PCB embodiments. The radiation mask 10' of FIGS. 8B and 8C includes a substrate 64 supporting at least one first segment 12A' and at least one second segment 12B'. The first segment 12A' and a second segment 12B' of the radiation mask 10' may be sized to selectively attenuate the radiation 16 for the first sectional area 26A' and the second sectional area 26B' of the PCB 22', respectively. The materials 43A', 43B' of the first segment 12A' and a second segment 12B' of the radiation mask 10' may also be different to provide selective attenuation when passing the radiation 16. Moreover, the substrate 64 may be relatively transmissive to the radiation 16, so that the radiation 16 may be substantially non-attenuated by the substrate 64. In this manner, the radiation 16 may be selectively attenuated for the PCB 22'.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In view of the foregoing, the scope of the present disclosure is determined by the claims that follow.

We claim:

1. A method for inspecting a printed circuit board (PCB), comprising:
    providing the PCB comprising a first sectional area including at least one sensitive semiconductor device, and a second sectional area which is free of a sensitive semiconductor device;
    disposing a radiation mask between an x-ray radiation source and the PCB, the radiation mask including a first segment and a second segment, wherein a thickness of the first segment is thicker than a thickness of the second segment, and wherein the thickness of the first segment is based on an average drain current leakage change associated with the at least one sensitive semiconductor device of less than one (1) percent resulting after at least two (2) radiation inspections;
    emitting, from the x-ray radiation source, a first portion of x-ray radiation towards the first sectional area and a second portion of the x-ray radiation towards the second sectional area, wherein the first portion passes through the first segment that attenuates the first portion at a first attenuation level, and wherein the second portion passes through the second segment substantially non-attenuated or attenuated at a second attenuated level which is less than the first attenuation level; and
    receiving, with a defect identification unit, a transmitted portion of the x-ray radiation that passed through the PCB.

2. The method of claim 1, wherein the PCB includes a circuit element whose function is sensitive to x-ray radiation.

3. The method of claim 1, wherein the disposing the radiation mask further includes positioning the first segment and the second segment a distance from the PCB, the distance being in a range from two (2) millimeters to fifteen (15) millimeters.

4. The method of claim 1, wherein the emitting the x-ray radiation comprises emitting the x-ray radiation having energy in a range from five (5) keV to one-hundred twenty-five (125) keV.

5. The method of claim 1, further comprising passing, free of attenuation or substantially free of attenuation, through at least one passageway of the radiation mask, a third portion of the x-ray radiation.

6. The method of claim 5, wherein the disposing the radiation mask includes disposing the first segment proximate to the first sectional area of the PCB and the second segment proximate to the second sectional area of the PCB.

7. The method of claim 1, wherein the thickness of the first segment is in a range from one (1) millimeter to fifteen (15) millimeters.

8. The method of claim 1, wherein the disposing the radiation mask further includes the thickness of the second segment being in a range from two-hundred (200) microns to fifteen (15) millimeters.

9. An inspection system for a printed circuit board (PCB), comprising:
    at least one standup configured to removably interface with the PCB;
    an x-ray radiation source configured to emit x-ray radiation towards the PCB, wherein the PCB includes a first sectional area that includes at least one sensitive semiconductor device, and wherein the PCB includes a second sectional area that is free of any sensitive semiconductor device;
    a radiation mask disposed between the x-ray radiation source and the PCB, the radiation mask including:
        a first segment configured to attenuate a first portion of the x-ray radiation emitted from the x-ray radiation source toward the first sectional area of the PCB with a first attenuation level; and
        a second segment configured to pass a second portion of the x-ray radiation emitted from the x-ray radiation source toward the second sectional area of the PCB with a second attenuation level, wherein the second attenuation level is less than the first attenuation level, wherein the second segment has a thickness, and wherein the radiation mask is oriented with the first segment between the radiation source and the first sectional area of the PCB and the second segment between the x-ray radiation source and the second sectional area when the x-ray radiation source emits the x-ray radiation; and a defect identification unit configured to receive a transmitted portion of the x-ray radiation that passed through the PCB.

10. The system of claim 9, wherein a thickness of the first segment is thicker than the thickness of the second segment of the radiation mask.

11. The system of claim 9, wherein the first segment comprises a different material than the second segment.

12. The system of claim 9, wherein the radiation mask further includes at least one passageway configured to receive a third portion of the x-ray radiation emitted towards a third sectional area of the PCB and to pass the third portion free from attenuation to the third sectional area of the PCB.

13. The system of claim 9, wherein the first segment and the second segment are configured to be disposed proximate to the PCB.

14. The system of claim 9, wherein the at least one standup is configured to position the first segment and the second segment a distance from the PCB, the distance being in a range from two (2) millimeters to fifteen (15) millimeters.

15. The system of claim 9, wherein a thickness of the first segment is based on an average drain current leakage change associated with the at least one sensitive semiconductor device of less than one percent resulting after at least two x-ray radiation inspections.

* * * * *

UNITED STATES PATENT AND TRADEMARK OFFICE
CERTIFICATE OF CORRECTION

PATENT NO. : 9,869,643 B2  
APPLICATION NO. : 14/163756  
DATED : January 16, 2018  
INVENTOR(S) : ShiJie Wen et al.

Page 1 of 1

It is certified that error appears in the above-identified patent and that said Letters Patent is hereby corrected as shown below:

On the Title Page

In item (54), and in the Specification, Column 1, Line 1, in "Title", delete "ATTENTUATE" and insert -- ATTENUATE --, therefor.

Signed and Sealed this  
Third Day of April, 2018

Andrei Iancu  
*Director of the United States Patent and Trademark Office*